United States Patent
Cope et al.

(10) Patent No.: US 8,579,118 B2
(45) Date of Patent: Nov. 12, 2013

(54) METHOD FOR PREPARING EARS OF CORN FOR AUTOMATED HANDLING, POSITIONING AND ORIENTING

(75) Inventors: Jason Cope, Ankeny, IA (US); David Kurth, Grimes, IA (US); Thomas Edwin Arneson, Marshalltown, IA (US); Kirk David Shirar, Marshalltown, IA (US); Kevin Ray Zaruba, Albion, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 244 days.

(21) Appl. No.: 12/545,298

(22) Filed: Aug. 21, 2009

(65) Prior Publication Data
US 2010/0209576 A1     Aug. 19, 2010

Related U.S. Application Data

(60) Provisional application No. 61/153,543, filed on Feb. 18, 2009.

(51) Int. Cl.
    *B07C 5/36*     (2006.01)
(52) U.S. Cl.
    USPC ............................................. 209/607
(58) Field of Classification Search
    USPC ............................................. 209/607
    See application file for complete search history.

(56) References Cited

U.S. PATENT DOCUMENTS

| | | | |
|---|---|---|---|
| 1,456,826 A * | 5/1923 | Peahotzki | 209/607 |
| 1,666,933 A * | 4/1928 | Hansen | 209/607 |
| 1,834,047 A * | 12/1931 | Chapman | 209/44.3 |
| 1,904,740 A * | 4/1933 | Lewis | 209/44.1 |
| 1,908,219 A * | 5/1933 | Chapman | 209/607 |
| 2,029,344 A | 2/1936 | Sheldon | |
| 2,115,107 A * | 4/1938 | Hoffeld | 209/23 |
| 2,257,470 A * | 9/1941 | Marchant | 209/607 |
| 2,675,942 A | 4/1954 | Vogelsang | |
| 2,875,942 A | 3/1959 | Wilson | |
| 3,195,485 A | 7/1965 | Reynolds | |
| 3,344,769 A | 10/1967 | Williams | |
| 3,348,780 A | 10/1967 | Barkstrom et al. | |
| 3,363,486 A | 1/1968 | Tourison | |

(Continued)

FOREIGN PATENT DOCUMENTS

| | | |
|---|---|---|
| AR | 073121 | 8/2009 |
| AR | 073196 | 8/2009 |

(Continued)

OTHER PUBLICATIONS

Anonymous. E-Z Creamer. Available at: http://www.agrisupply.com/product.asp?pn=75436#tips accessed Aug. 27, 2011.*

(Continued)

*Primary Examiner* — Wendy C Haas
(74) *Attorney, Agent, or Firm* — Ballard Spahr LLP (57) ABSTRACT

A method for automated handling, positioning and orienting of an ear of corn includes methods for altering a portion of an ear of corn. Optionally included are one or more stations for automatically processing, testing, sampling and preparing the ear of corn for processing, testing or sampling and an automated transport means for automatically moving ears of corn from station to station using alterations made to the ear of corn.

23 Claims, 5 Drawing Sheets

(56) References Cited

U.S. PATENT DOCUMENTS

| | | |
|---|---|---|
| 3,394,805 A * | 7/1968 | Ross et al. .................. 209/539 |
| 3,460,492 A | 8/1969 | Dickinson, III et al. |
| 3,530,372 A | 9/1970 | Laukien |
| 3,572,548 A | 3/1971 | Fuchs |
| 3,592,249 A | 7/1971 | Ross |
| 3,685,519 A | 8/1972 | Cover et al. |
| 3,741,793 A | 6/1973 | Simmons |
| 3,830,902 A | 8/1974 | Barnes |
| 3,831,736 A | 8/1974 | Barnes |
| 3,884,347 A | 5/1975 | Gallagher et al. |
| 3,921,459 A | 11/1975 | Willett |
| 3,930,212 A | 12/1975 | Ioffe et al. |
| 3,991,704 A | 11/1976 | Hulstein et al. |
| 4,230,983 A | 10/1980 | Steere et al. |
| 4,238,658 A | 12/1980 | Kalnin et al. |
| 4,278,625 A | 7/1981 | Dedolph |
| 4,300,462 A | 11/1981 | Wilkins et al. |
| 4,301,762 A | 11/1981 | Burnett, Jr. |
| 4,413,014 A | 11/1983 | Melancon |
| 4,436,207 A | 3/1984 | Klukis |
| 4,602,716 A | 7/1986 | Barla-Szabo et al. |
| 4,753,159 A | 6/1988 | Eaton |
| 5,097,625 A | 3/1992 | Kaneko et al. |
| 5,238,121 A | 8/1993 | Frisbie |
| 5,677,474 A | 10/1997 | Rogers |
| 6,299,368 B1 | 10/2001 | Tavularis |
| 6,307,123 B1 | 10/2001 | Kriz et al. |
| 6,409,007 B1 | 6/2002 | Malon |
| 6,537,826 B1 | 3/2003 | Horigane |
| 6,659,338 B1 | 12/2003 | Dittmann et al. |
| 6,705,827 B2 | 3/2004 | Keller et al. |
| 6,706,989 B2 | 3/2004 | Hunter et al. |
| 6,809,819 B1 | 10/2004 | Vinjamoori et al. |
| 6,865,556 B2 | 3/2005 | Penner et al. |
| 6,872,136 B1 * | 3/2005 | Bennett ..................... 460/51 |
| 6,959,617 B2 | 11/2005 | Deppermann |
| 7,024,817 B2 | 4/2006 | Zehner et al. |
| 7,043,070 B2 | 5/2006 | Vilella |
| 7,044,306 B2 | 5/2006 | Deppermann et al. |
| 7,067,834 B2 | 6/2006 | Horigane et al. |
| 7,197,374 B2 | 3/2007 | Silverbrook et al. |
| 7,207,485 B2 | 4/2007 | Silverbrook et al. |
| 7,290,665 B2 | 11/2007 | Hunter et al. |
| 7,367,155 B2 | 5/2008 | Kotyk et al. |
| 7,502,113 B2 | 3/2009 | Deppermann et al. |
| 7,588,151 B2 | 9/2009 | Hunter et al. |
| 7,591,101 B2 | 9/2009 | Deppermann et al. |
| 7,591,374 B2 | 9/2009 | Hunter et al. |
| 7,600,642 B2 | 10/2009 | Deppermann et al. |
| 7,611,842 B2 | 11/2009 | Deppermann et al. |
| 7,685,768 B2 | 3/2010 | Deppermann et al. |
| 7,703,238 B2 | 4/2010 | Deppermann et al. |
| 7,735,626 B2 | 6/2010 | Cope et al. |
| 7,767,883 B2 | 8/2010 | Deppermann et al. |
| 7,830,516 B2 | 11/2010 | Deppermann et al. |
| 7,832,143 B2 | 11/2010 | Deppermann et al. |
| 7,849,632 B2 | 12/2010 | Deppermann et al. |
| 7,877,926 B2 | 2/2011 | Deppermann et al. |
| 7,905,050 B2 | 3/2011 | Hunter et al. |
| 7,915,006 B2 | 3/2011 | Cope et al. |
| 7,934,600 B2 | 5/2011 | Deppermann et al. |
| 7,941,969 B2 | 5/2011 | Deppermann et al. |
| 7,997,415 B2 * | 8/2011 | Mongan et al. ............. 209/213 |
| 7,998,669 B2 | 8/2011 | Deppermann et al. |
| 8,028,469 B2 | 10/2011 | Deppermann et al. |
| 8,031,910 B2 | 10/2011 | Jones et al. |
| 8,071,845 B2 | 12/2011 | Deppermann et al. |
| 8,076,076 B2 | 12/2011 | Osborn et al. |
| 8,245,439 B2 | 8/2012 | Deppermann et al. |
| 8,281,935 B2 | 10/2012 | Deppermann et al. |
| 2003/0070567 A1 | 4/2003 | Thomas |
| 2004/0267457 A1 | 12/2004 | Timmis et al. |
| 2005/0210744 A1 | 9/2005 | Watanabe et al. |
| 2006/0042527 A1 | 3/2006 | Deppermann |
| 2006/0046244 A1 | 3/2006 | Deppermann et al. |
| 2006/0046264 A1 | 3/2006 | Deppermann et al. |
| 2006/0048247 A1 | 3/2006 | Deppermann |
| 2006/0048248 A1 | 3/2006 | Deppermann |
| 2006/0222958 A1 | 10/2006 | Yamaguchi et al. |
| 2007/0048872 A1 | 3/2007 | Deppermann et al. |
| 2007/0204366 A1 | 8/2007 | Deppermann et al. |
| 2007/0207485 A1 | 9/2007 | Deppermann et al. |
| 2008/0131254 A1 | 6/2008 | Cope et al. |
| 2008/0131924 A1 | 6/2008 | Cope et al. |
| 2008/0317279 A1 | 12/2008 | Deppermann et al. |
| 2009/0061449 A1 | 3/2009 | Chung et al. |
| 2009/0155878 A1 | 6/2009 | Becker et al. |
| 2009/0215060 A1 | 8/2009 | Deppermann et al. |
| 2010/0044356 A1 | 2/2010 | Cope |
| 2010/0086963 A1 | 4/2010 | Deppermann et al. |
| 2010/0209228 A1 * | 8/2010 | Cope et al. ................. 414/788.7 |
| 2010/0299790 A1 | 11/2010 | Deppermann et al. |
| 2011/0081716 A1 | 4/2011 | Deppermann et al. |
| 2011/0117570 A1 | 5/2011 | Cope et al. |
| 2011/0129836 A1 | 6/2011 | Deppermann et al. |
| 2011/0160068 A1 | 6/2011 | Becker et al. |
| 2011/0217700 A1 | 9/2011 | Deppermann et al. |
| 2011/0225680 A1 | 9/2011 | Cope |
| 2011/0296930 A1 | 12/2011 | Deppermann et al. |
| 2012/0079629 A1 | 3/2012 | Deppermann et al. |
| 2012/0180386 A1 | 7/2012 | Deppermann et al. |

FOREIGN PATENT DOCUMENTS

| | | |
|---|---|---|
| CN | 102325606 | 8/2009 |
| CN | 102325607 | 8/2009 |
| DE | 196 16 216 A1 | 10/1997 |
| EP | 0611604 A3 | 8/1994 |
| EP | 1 126 268 A1 | 8/2001 |
| EP | 1 346 206 B1 | 9/2003 |
| EP | 1 391 713 A2 | 2/2004 |
| EP | 2395600 | 8/2009 |
| EP | 2398599 | 8/2009 |
| GB | 2 293 744 A | 4/1996 |
| GB | 2293744 A | 4/1996 |
| KR | 10-2000-0022775 | 11/2001 |
| KR | 339689 B | 6/2002 |
| RU | 1805835 A3 | 3/1993 |
| RU | 2187919 C2 | 8/2002 |
| WO | WO-80/01531 A1 | 8/1980 |
| WO | WO/03/084847 | 10/2003 |
| WO | WO 03/084847 A2 | 10/2003 |
| WO | WO-03/100381 A1 | 12/2003 |
| WO | WO/2006/026466 | 3/2006 |
| WO | WO 2006/026466 A2 | 3/2006 |
| WO | WO/2006/026467 | 3/2006 |
| WO | WO 2006/026467 A2 | 3/2006 |
| WO | WO/2007/025250 | 3/2007 |
| WO | WO 2007/025250 A2 | 3/2007 |
| WO | WO/2007/103769 | 9/2007 |
| WO | WO-2007/103769 A2 | 9/2007 |
| WO | WO 2007/103769 A2 | 9/2007 |
| WO | WO/2007/103786 | 9/2007 |
| WO | WO-2007/103786 A2 | 9/2007 |
| WO | WO 2007/103786 A2 | 9/2007 |
| WO | WO/2008/150798 | 12/2008 |
| WO | WO-2008/150798 A1 | 12/2008 |
| WO | WO 2008/150798 A1 | 12/2008 |
| WO | WO/2009/032741 | 3/2009 |
| WO | WO 2009/032741 A2 | 3/2009 |
| WO | PCT/US2009/054644 | 8/2009 |
| WO | PCT/US2009/054650 | 8/2009 |

OTHER PUBLICATIONS

International Search Report for related International Appl. No. PCT/US2007/084583, mailed Feb. 10, 2008.

International Search Report for related International Appl. No. PCT/US2008/086992, mailed Jul. 9, 2009.

Leung et al., "Performance Analysis of Automatic Assembly Systems with In-Line Parallel Stations," *IMA Journal of Mathematics Applied in Business & Industry*, 1997, vol. 8, No. 1, pp. 1-22.

Krone, Todd L., "Genetic Analysis and Breeding for Kernel Methionine Content in Maize (Zea Mays L.)," *Thesis submitted in*

(56) References Cited

OTHER PUBLICATIONS partial fulfillment of requirements for the degree of Doctor of Philosophy, University of Minnesota, Aug. 1994.

Sangtong et al., "Serial Extraction of Endosperm Drillings (SEED)—A Method of Detecting Transgenes and Proteins in Single Viable Maize Kernels," *Plant Molecular Biology Reporter*, vol. 19, Jun. 2001, pp. 151-158.

International Search Report and Written Opinion, issued in connection with corresponding International Application No. PCT/US2009/054644, mailed Feb. 3, 2010.

Aitken-Christie, J. et al., *Automation in Plant Tissue Culture*, Automation and Environmental Control in Plant tissue Culture (1995) 1-18.

Casady, W. W. et al., *An Automated Kernel Positioning Device for Computer Vision Analysis of Grain*, American Society of Agricultural Engineers, vol. 32(5) (1989) 1821-1826.

Chunwongse, J. et al., *Pre-Germation Genotypic Screening Using PCR Amplification of Half-Seeds*, Theor Appl Genet, 86 (1993) 694-698.

Churchill, D. B. et al., *Rotating Table for Measuring Seed Physical Properties*, Transactions of the ASAE, vol. 34(4) (1991) 1842-1845.

Dekkers, J. C. M. et al., *The Use of Molecular Genetics in the Improvement of Agricultural Populations*, Nature Reviews | Genetics, vol. 3, (2002) 22-32.

Gasvoda, D. et al., *Whiteback Pine Seed Scarifier*, United States Department of Agriculture Food Service, Technology & Development Program, Timber Tech Tips, 0224-2332-MTDC (2002) pp. 1-6.

Hahnen, S. et al., *Automated DNA Preparation from Maize Tissues and Food Samples Suitable for Real-time PCR Detection of Native Genes*, European Food Research Technology, vol. 215 (2002) 443-446.

Higley, P.M., et al., *Effects of Non-Destructive Tissue Extraction on the Viability of Corn, Soybean and Bean Seeds*, Seed Sci. & Technol., 22 (1994) 245-252.

Horigane, A. et al., *Evaluation of Color Characteristics of Cross-Sectioned Wheat Kernels*, Food Sci. Technol. Res., 9:4 (2003), 327-331.

Horigane, A. et al., *Measurement of Brightness of Cross-Sectioned Wheat Kernels*, Japanese Journal of Crop Science, vol. 72, (attachment No. 1) (2003) 176-177.

Horigane, A. et al., *Two-Dimensional Analysis of Kernels Using a New Sample Preparation Method*, Chemistry and Biology, vol. 41, No. 6 (2003) 398-402.

Kamiya, M. et al., *Rapid DNA Extraction Method from Soybean Seeds*, Breeding Science 53 (2003) 277-279.

Kang, H.W. et al., *A Rapid DNA Extraction Method for RFLP and PCR Analysis from a Single Dry Seed*, Plant Molecular Biology Reporter, 16:90 (1998) 1pg.

Kerk, N.M. et al., *Laser Capture Microdissection of Cells from Plant Tissues*, Plant Physiology, vol. 132 (2003) 27-35.

Krysan, P., *Ice-Cap. A High-Throughput Method for Capturing Plant Tissue Samples for Genotype Analysis*, Plant Physiology, vol. 135 (2004) 1162-1169.

Liu, W. et al., *Highly Efficient Doubled-Haploid Production in Wheat via Induced Microsphere Emblyogenesis*, Crop Science, vol. 42 (2002) 686-692.

McCarthy, P. L. et al., *Rapid Identification of Transformed Wheat Using a Half-Seed PCR Assay*, BioTechniques 32 (2002) 560-564.

Pearson, T.C. et al., *Reduction of Aflatoxin and Fumonisin Contamination in Yellow Corn by High-Speed Dual-Wavelength Sorting*, Cereal Chem. 81(4), (2004) 490-498.

Peterhansel, C. et al., *Quantitative Detection of Transgenic and Endogenous DNA Sequences in Seeds After Automated DNA Preparation*, Biomed. Eng. Appl. Basis Commun. 16 (2004) 1-6.

Rafalski, J. A., *Genetic Diagnostics in Plant Breeding: RAPDs Microsatellites & Machines*, TIG, vol. 9, No. 8 (Aug. 1993) 275-280.

Sangtong, V. et al., *Serial Extraction of Endosperm Drillings (SEED)—A Method for Detecting Transgenes and Proteins in Single Viable Maize Kernels*, Plant Molecular Biology Reporter 19 (2001) 151-158.

Skinner, D. Z. et al., *Segregation and Conditioning Probability Association of Molecular Markers With Traits in Autotetraploid Alfalfa*, Molecular Breading, vol. 5 (2000) 295-306.

Smith, J. S. C. et al., *Genetic Purity and Testing Technologies for Seed Quality: A Company Perspective*, Seed Science Research 8 (1998) 285-293.

Sweeney, P. et al., *Random Amplified Polymorphic DNA Analysis of Dry Turfgrass Seed*, HortScience 31(3), (1996) 400-401.

Turner, N. A., et al., *Sampling and Analysis for Determining Relationship of Calcium Concentration to Bitter Pit in Apple Fruit*, New Zealand Journal of Agricultural Research 20:4 (1977) 525-532.

Von Post, R. et al., *A High-throughput DNA Extraction Method for Barley Seed*, Euphytica, 130 (2003) 255-260.

Wang, G.L., et al., *PCR Amplification from Single Seeds, Facilitating DNA Marker-Assisted Breeding*, Nucleic Acids Research 21(10), (1993) 2527.

Wenxue, Z., et al., *PCR Analysis of Half-Seeds of Cereal Crops and Its Applications in Marker-assisted Selection and breeding*, Chinese Journal of Biotechnology, 12:4 (1997) 249-255.

Xu, Y., *Developing Marker-Assisted Selection Strategies for Breeding Hybrid Rice*, Plant Breeding Review, 23 (2003) 73-174.

Yang, W, et al., *A Preliminary Study of Non-Lethal Specific Sampling of Corn Embryo and Endosperm and Feasibility of Automating the Seed Selection Process Utilizing the Specific Sampling Technique*, Pioneer Hi-Bred (2002) 1-41.

Wang, J. et al., *Identification of Parents of F1 Hybrids Through SSR Profiling of Material and Hybrid Tissue*, Euphytica, vol. 124 (2004) 29-43.

Yao, Y., et al., *Single Kernel Sampling Method for Maize Starch Analysis While Maintaining Kernel Vitality*, Cereal Chem. 79:6 (2002) 757-762.

DuPont CoatingSolutions [online] [retrieved Apr. 4, 2013]. Retrieved from the Internet: <URL: www.ccaiweb.com/PDF/MembersOnly/annualpres08/DuPontCoatingSolutions - Corporate Member Presentation.pdf>. (undated) 12 pages.

200 watt CO2 laser from Synrad provides the best cost per delivered watt available in today . . . [online] [retrieved Dec. 18, 2012]. Retrieved from the Internet: <URL: http://www.synrad.com/fseries/f201.htm>. (2011) 2 pages.

Skinner, D. Z. et al., *Segregation and Conditioning Probability Association of Moleculat Markers With Traits in Autotetraploid Alfalfa*, Molecular Breeding, vol. 6 (2000) 295-306.

U.S. Appl. No. 12/545,298, filed Aug. 21, 2009, Cope, et al.

U.S. Appl. No. 13/618,938, filed Sep. 14, 2012, Cope, et al.

International Preliminary Report on Patentability issued on Aug. 23, 2011 for PCT/US2009/054644, which was filed on Aug. 21, 2009 [Inventor—Cope; Applicant—Pioneer Hi-Bred International, Inc.] [6 pages].

International Preliminary Report on Patentability issued on Aug. 23, 2011 for PCT/US2009/054650, which was filed on Aug. 21, 2009 [Inventor—Cope; Applicant—Pioneer Hi-Bred International, Inc.] [5 pages].

International Search Report issued on Feb. 3, 2010 for PCT/US2009/054650, which was filed on Aug. 21, 2009 [Inventor—Cope; Applicant—Pioneer Hi-Bred International, Inc.] [3 pages].

Written Opinion issued on Jan. 29, 2010 for PCT/US2009/054650, which was filed on Aug. 21, 2009 [Inventor—Cope; Applicant—Pioneer Hi-Bred International, Inc.] [4 pages].

* cited by examiner

METHOD FOR PREPARING EARS OF CORN FOR AUTOMATED HANDLING, POSITIONING AND ORIENTING

RELATED APPLICATIONS

This application claims priority under 35 U.S.C. §119 to provisional application Ser. No. 61/153,543 filed Feb. 18, 2009, which application is hereby incorporated by reference in its entirety.

FIELD OF THE INVENTION

The present invention relates to handling, positioning and orienting ears of corn. More particularly, the present invention relates to automated, high-throughput methods for altering ears of corn to provide for automated handling, positioning and orienting of the ear.

BACKGROUND

Methods for handling, positioning and/or orienting ears of corn for sampling purposes has been predominantly accomplished using manual techniques. Most manual techniques require unnecessary amounts of human involvement, which invariably limits the overall efficiency of the process. As companies try to conserve resources, time, money and manpower, techniques for automating processes otherwise performed manually are of increasing importance.

As more and more corn sampling methods and processes are automated, what is needed is an efficient and high-throughput handling, positioning and orienting method for an ear of corn.

Therefore, it is a primary object, feature, or advantage of the present invention to improve over the state of the art.

It is a further object, feature, or advantage of the present invention to provide a method for high-throughput handling, positioning and orienting of an ear of corn.

Another object, feature, or advantage of the present invention is to provide for an easy and safe method for preparing an ear of corn for automated handling, positioning and orienting.

A still further object, feature, or advantage of the present invention is to provide methods for preparing an ear of corn for being handled, positioned and oriented in automated ear preparation and sampling processes.

Yet another object, feature, or advantage of the present invention is to provide a method for preparing an ear of corn for being handled, positioned and oriented by automation.

A still further object, feature, or advantage of the present invention is to provide a method for preparing an ear of corn for being handled, positioned and oriented by automation that automatically accounts for size and shape differences between each ear of corn.

Yet another object, feature, or advantage of the present invention is to provide a method for preparing an ear of corn for being handled, positioned and oriented by automation which is user friendly, and safe to operate.

A still further object, feature, or advantage of the present invention is to provide a method for preparing an ear of corn for being handled, positioned and oriented by automation which can be operated and performed by a single operator.

These and/or other objects, features, or advantages of the present invention will become apparent. No single embodiment of the present invention need achieve all or any particular number of the foregoing objects, features, or advantages.

BRIEF SUMMARY

The invention generally provides an automated method for preparing an ear of corn for being handled, positioned and/or oriented by one or more automated processes.

According to one aspect of the present invention, a method for preparing an ear of corn for being handled, positioned and/or oriented by automated means is disclosed. The method includes providing a station for altering an ear of corn, keeping the ear of corn in a desired position and orientation at the station and altering the ear of corn. The altering step includes removing tissue from the ear of corn or appending material to the ear of corn to provide for automated handling, positioning and/or orienting of the ear of corn.

According to another aspect of the present invention, a method for automated handling, positioning and orienting of an ear of corn by conveyance means in a high-throughput system is disclosed. The method includes the steps of providing a station for altering an ear of corn, holding the ear of corn at the station during altering, altering the ear of corn to have a feature used to secure the ear of corn to the conveyance means, and handling, positioning and orienting the ear of corn in the high-throughput system using the conveyance means for testing, sampling, processing or preparing the ear of corn for testing, sampling or processing.

DETAILED DESCRIPTION OF THE PREFERRED EMBODIMENT

The following description is merely exemplary in nature and is not intended to limit the present disclosure, application, or uses. For a better understanding of the invention, several exemplary embodiments will now be described in detail. Reference will be taken from time to time to the appended drawings. Reference numerals will be used to indicate certain parts or locations in the drawings. These same reference numerals will indicate the same parts or locations throughout the drawings, unless otherwise indicated.

Apparatus

Figure 1:
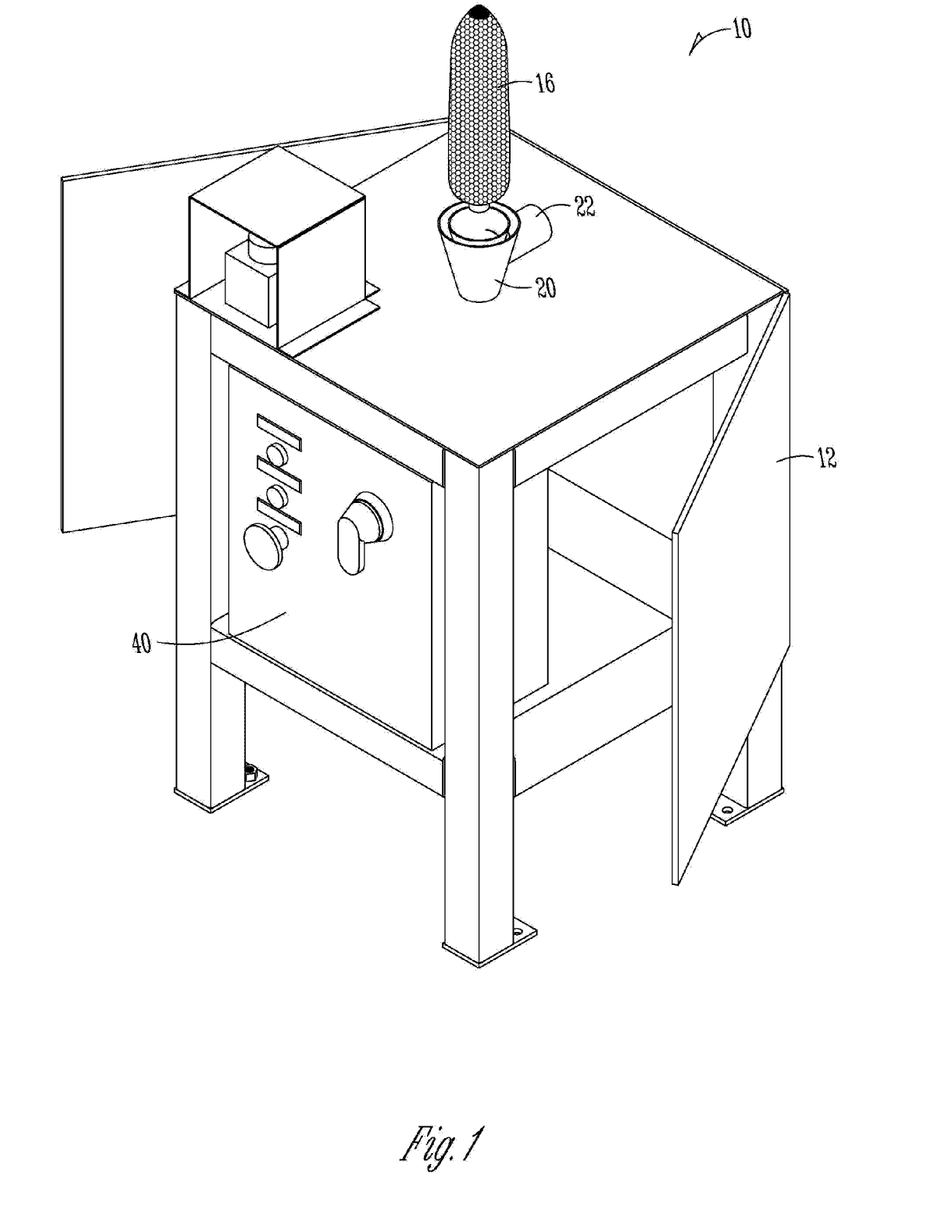
FIG. 1 is a perspective view of the invention.

The present invention discloses in one aspect an apparatus for preparing an ear of corn for being handled, positioned and oriented by automation. One embodiment of apparatus 10 is shown in FIG. 1. Apparatus 10 may be in the form of a station having at least the ability to alter an ear of corn for being handled, positioned and oriented by automation. Apparatus 10 may be partially or fully enclosed within cabinet 12; alternatively, a frame or other supporting members may be fashioned, alone or in combination with another system for holding the various components of apparatus 10. In a preferred form, apparatus 10 includes some holding means adapted for keeping the ear of corn in a desired position and orientation. The holding means may be full or semi-automated holding means. The present invention contemplates that the holding means could include any type of mechanical device that applies positive pressure to the ear of corn to keep the ear of corn in a desired position and orientation. Such mechanical devices may include grips, clamps, irises, a chuck, an expandable bladder or any other mechanical means for gripping or holding an ear of corn by the shank or some other portion of the ear. Other holding means are contemplated herein, such as pneumatic devices that generate a negative pressure (i.e., a vacuum) to keep the ear of corn in a desired position and orientation. One example of a pneumatic holding means is illustrated FIGS. 1-3, which show a conofrustical recess 20. Recess 20 is in operable communication with a vacuum to provide negative pressure or a vacuum force at the conofrustical recess 20 for retaining the ear of corn 16 in a desired position and orientation. Contemplation has also been given to holding means, such as support device that includes one or more support members for resting the ear of corn thereon. For example, rails, tubing or other guide members could be used to orient and keep the ear of corn in a desired position or orientation at apparatus 10 during altering. In the preferred form, the holding means provides for automated high-throughput positioning and orienting of ears of corn at apparatus 10.

According to a preferred form of the present invention, apparatus 10 also includes altering means. Generally, the altering means provides some automated alteration of the ear of corn to allow for automated handling, positioning and orienting of the ear of corn. The altering means may be configured to alter each ear of corn by appending material to or removing material (tissue) from the ear of corn. For example, a tissue removal device having tissue removal means may be used for preparing a portion of the ear of corn to provide for automated handling, positioning and/or orienting of the ear of corn. Alternatively, a material appendage device having material appendage means may be used for preparing a portion of the ear of corn to provide for automated handling, positioning and/or orienting of the ear of corn. Depending on the desired type of alteration, apparatus 10 may include one or both types of altering means. In the case where apparatus 10 includes tissue removal means, contemplation is given in the present invention to an automated scraping tool having one or more edges for scrapping material from the ear of corn, an automated erosion tool having one or more liquid jets for eroding material from the ear of corn, or an automated cutting tool having one or more blades for cutting material from the ear of corn. In the case where material, such as ear tissue, is removed from the ear of corn, any of the aforementioned concepts may be used to create a hole or void in the ear of corn or clear tissue from a portion of the ear to provide a spot for holding the ear of corn. Boring a hole in the shank of the ear of corn or removing tissue (i.e., kernels) from the ear of corn may be accomplished specifically by using a drill bit, router bit, forstner bit, hollow boring tube, liquid jet cutter, or chisel. According to one aspect of the present invention, a pneumatically actuated drill (see FIG. 4) may be used to create a hole in the shank of the ear of corn. In the case where material is being appended to an ear of corn, apparatus 10 may include an automated device adapted to append a member or material to the ear of corn to provide for automated positioning, handling and/or orienting of the ear of corn using the appended material or member. Various types of materials or members could be appended to the ear of corn whereby some automated system could use the appended materials or members to position, handle and/or orient the ear of corn. Materials such as magnetically active coatings could be applied to a portion of the ear of corn (i.e., the shank portion) whereby an automated process or system uses the coating to grip or hold onto the ear of corn. Alternatively, rigid structural members such as spindle, post, nail, or screw could be inserted into a portion of the ear of corn whereby some automated system could use the member to position, handle and/or orient the ear of corn. For example, an automated drill or impacting device could be used to append such members as a post, spindle, screw or nail to the ear of corn. In a preferred form of the present invention, the altering means is actuated into the holding means. For example, as shown in FIGS. 1-4, drill 30 is actuated by piston 32 to engage ear of corn 16. The present invention also contemplates that the holding means could be actuated into the altering means.

Figure 5:
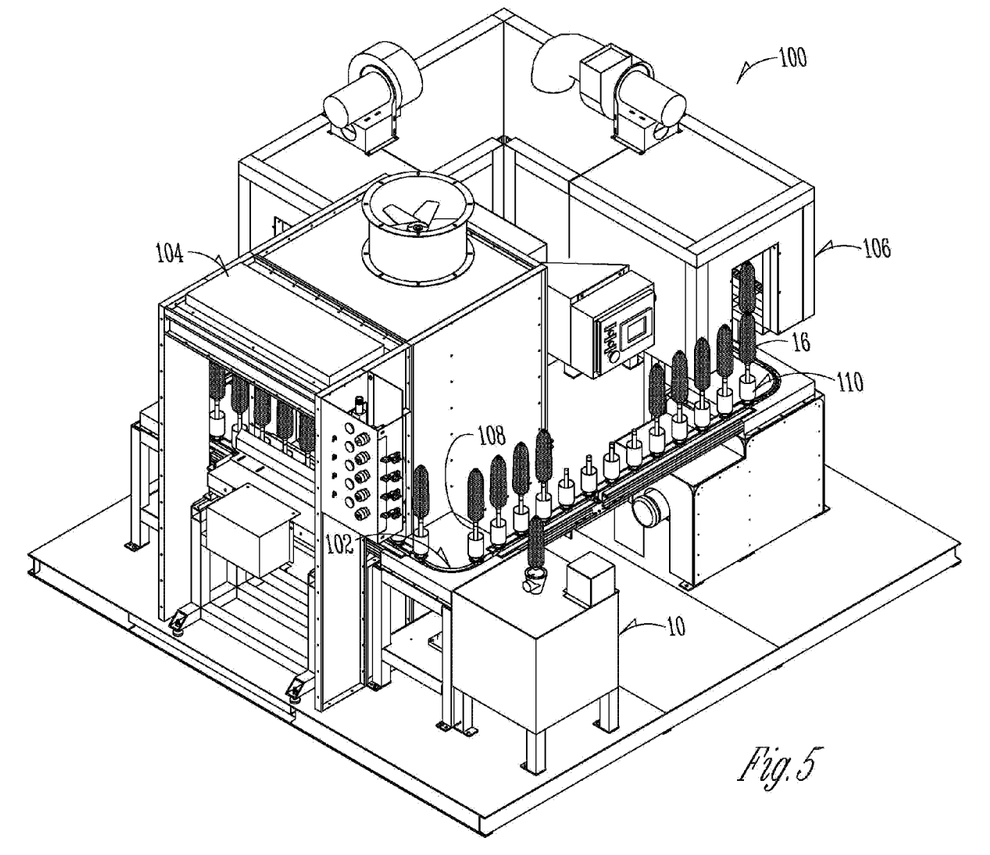
FIG. 5 is a perspective view of an exemplary embodiment of the invention.

As shown in FIG. 5, apparatus 10 may be used in combination with an automated system or process such as the "High Throughput Automated Apparatus, Method and System for Coating Ears of Corn" as shown and described in Provisional Application Ser. No. 61/090,979, filed Aug. 22, 2008, which application is assigned to the owner of the present application and incorporated by reference herein in its entirety. Automated system 100 may be configured for processing, testing or sampling the ear of corn. System 100 may also be configured for preparing the ear of corn for processing, testing or sampling. In the preferred configuration, automated system 100 would include some type of ear moving means for moving and/or positioning corn at and between stations. Alterations made to the ear of corn are configured to work in concert with the moving means, such as for example, where the ear moving means includes one or more features adapted to make use of the cavity, added material or appended structure to handle, position and/or orient the ear of corn by automation.

Figure 2:
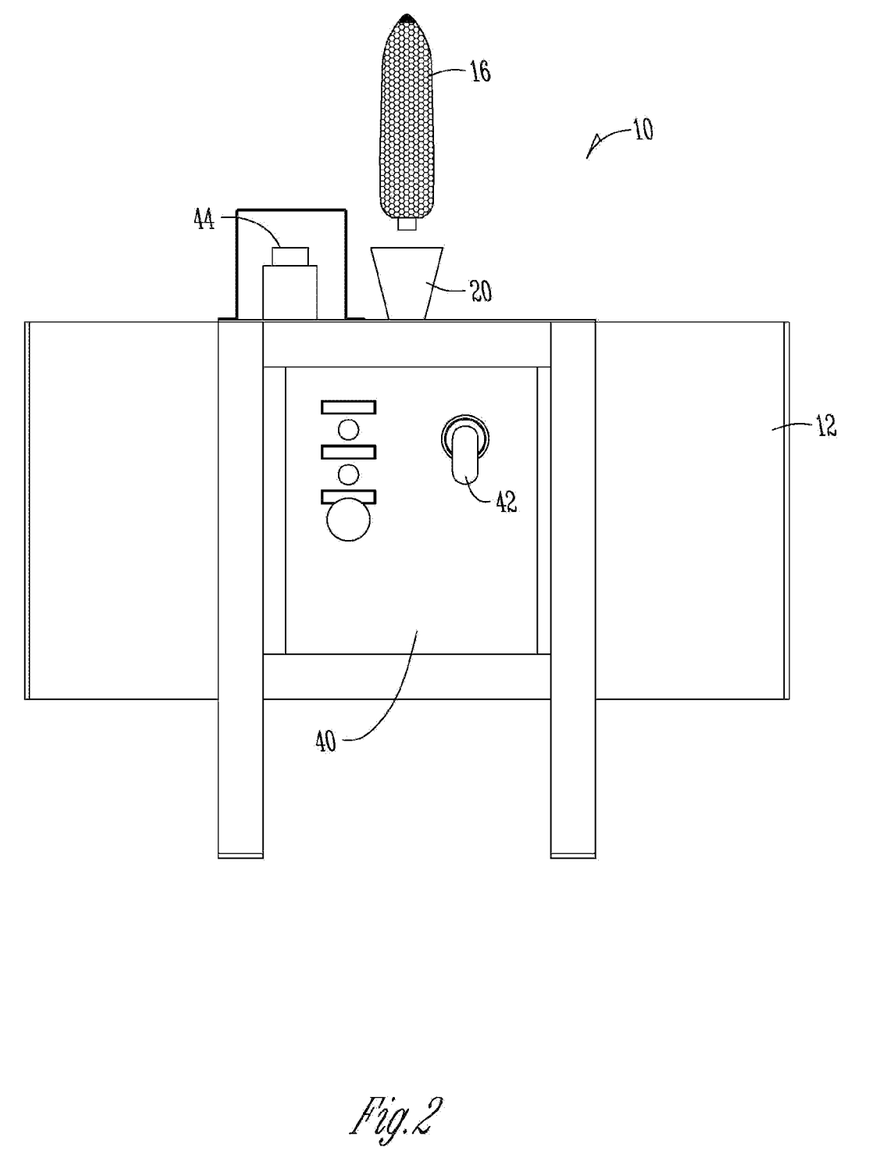
FIG. 2 is a front view of the invention.
Figure 3:
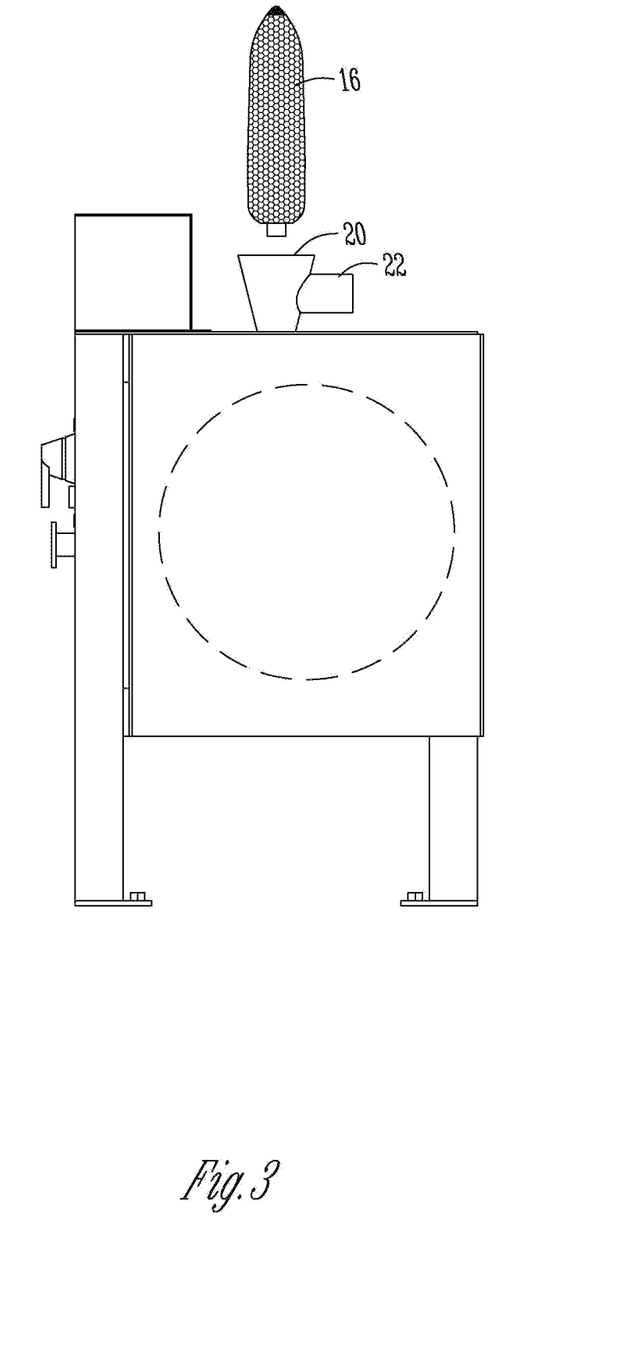
FIG. 3 is a side view of the invention.
Figure 4:
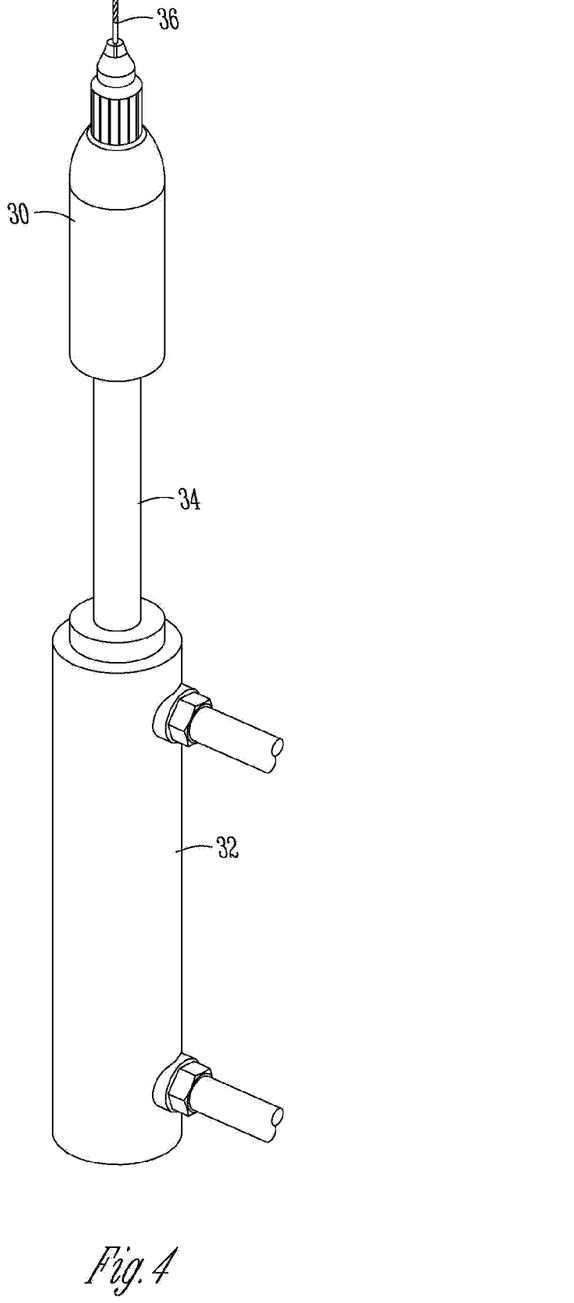
FIG. 4 is a cut away side view of the interior of the invention.

FIGS. 1-5 illustrate one exemplary embodiment configured to accomplish one or more of the objects, features or advantages of the present invention. FIG. 1 is a perspective view of apparatus 10 configured to alter an ear of corn 16 by tapping a hole into a portion of the ear of corn 16. The apparatus 10 generally comprises a cabinet 12 upon which is mounted a control panel 40 and includes holding means, such as a conofrustical recess 20 having a drill cuttings suction port 22. Within the interior of the cabinet 12, as shown in FIG. 4, is a tissue removal means, such as a drill 30 for drilling ear of corn 16 and piston 32 for advancing drill 30 and bit 36 into the shank or cob of ear of corn 16. The present invention also contemplates that the ear of corn 16 could be moved into contact with drill 30.

The conofrustical recess 20 has a cropped cone shape, as best shown in FIGS. 2 and 3, for self-centering of the ear of corn 16 relative to drill 30. The drill cuttings suction port 22, as shown in FIG. 3, is in operative communication with the conofrustical recess 20 so that as suction is provided at the drill cuttings suction port 22 the pressure differential is communicated to the conofrustical recess 20, thereby holding the ear of corn 16 in place. The drill cuttings suction port 22 removes cuttings and other debris from the conofrustical recess 20 as it is removed from the ear of corn 16 during the drilling process. The present invention is not limited to vacuum assisted retention of the ear of corn 16 within the conofrustical recess 20. The present invention contemplates that other holding means could be used, such as any one of the holding means discussed previously. For example, holding means may include positive-pressure, self-adjusting grips that would secure the ear of corn 16 by gripping the shank. Other considerations include, but are not limited to, counter screws for screwing into the shank or cob of the ear of corn 16 for securing the ear or an inflatable bladder within the conofrustical recess that surrounds and captures the shank of the ear of corn 16 when set in the conofrustical recess 20.

Also on cabinet 12 is a control panel 40, as shown in FIG. 2. Most importantly, the control panel includes a main disconnect 42 and a free hand safety switch 44. Additionally, a light sensor (not shown) in operative communication with the control panel may be included in the conofrustical recess 20 at the appropriate depth to ensure that the ear of corn 16 is seated properly within the conofrustical recess 20 before engaging the drill 30 or allowing the drill 30 and bit 36 to be advanced into the shank of the ear of corn 16. The sensor and free hand safety switch 44 provide adequate redundancy in safety to prevent the operator from accidentally coming into contact with drill bit 36. The control panel 40 may also include controls for adjusting the drilling speed and depth of the tap into the ear of corn 16. The main disconnect 42 is necessarily present so that power to the system can be disengaged for safety or maintenance purposes.

As shown in FIG. 4, apparatus 10 further includes a drill 30 and piston 32. The drill 30 is attached to the arm 34 of the piston so that the drill 30 and bit 36 may be raised or lowered to tap a hole into the shank of the ear of corn 16 using bit 36. Preferably, the drill 30 and piston 32 are pneumatically powered from a centralized source. The rotational speed of the drill bit 36 and depth to which the ear of corn 16 is tapped (the extension of piston 32) are monitored by an operator or electronically and controlled by the control panel 40. Drill 30 is preferably pneumatic (e.g., PAR-A-MATIC self-feed drill, model no. 8255-A, Winnipeg, Manitoba, Calif.) and pneumatically actuated by piston 32. Both drill 30 and piston 32 could be operated by a local or remote pneumatic pump. In the present invention, a hole is created in the shank of the ear of corn 16. Preferably, the hole in the ear of corn 16 is used for handling, positioning and/or orienting the ear of corn 16; however, the present invention contemplates that the hole created in the shank or cob of the ear of corn 16 could be used to inoculate the ear of corn 16. Apparatus 10 could also be used to drill out and collect samples (the cuttings and debris) from each ear of corn 16 for testing. The apparatus 10 of the present invention could be used in combination with any automated system, such as system 100 shown in FIG. 5, for processing, testing, sampling the ear of corn 16 and/or an automated machine for preparing the ear of corn 16 for processing, testing and/or sampling.

FIG. 5 illustrates one example of apparatus 10 functioning as a subsystem or station of an automated system 100, such as the "High Throughput Automated Apparatus, Method and System for Coating Ears of Corn" as shown and described in Provisional Application Ser. No. 61/090,979, filed Aug. 22, 2008, which application is assigned to the owner of the present application and incorporated by reference herein in its entirety. FIG. 5 illustrates but one embodiment of apparatus 10 functioning as a subsystem or station of an automated system. One purpose of apparatus 10, as can be seen from FIG. 5, is to prepare the ear of corn 16 for processing, testing and/or sampling by automation. Apparatus 10 may also be used in combination with one or more automated systems for processing, testing, sampling the ear of corn 16. By way of example, automated system 100 shown in FIG. 5 may include one or more types of automated transport means 102 for automatically moving ears of corn 16 from one processing station 104 to another processing station 106. The automated transport means 102 may also be used to provide automated positioning, handling and/or orientation of the ear of corn 16 to facilitate processing of the ear of corn 16 at each processing station 104, 106. The present invention contemplates that the automated transport means 102 could be any type of shuttle, carriage, or conveyor, such as a chain-on edge conveyor spindle or drive 110 shown in FIG. 5. The chain-on-edge conveyor spindle or drive 110 may include, for example, vertically oriented posts or spindles 108 intermittently spaced and attached along a continuous chain or belt that is cycled through one or more stations, such as processing stations 104, 106. Processing stations 104, 106 could be any station or subsystem providing automated processing, testing, sampling and/or preparing the ear of corn 16 for processing, testing and/or sampling. The processing stations could include an automated ear coating station for coating each ear of corn 16 with a magnetically active coating, and an automated drying station for curing the coating. The present invention contemplates other coatings for applying to the ear of corn, such as fungicides. Processing stations 104, 106 could also include any station or subsystem providing automated positioning of the coated kernels for seed testing. The kernels of corn separated from the cob could be positioned within the station collectively or individually using magnetic attenuation from a magnetic source. Using apparatus 10, as described above, holes are drilled into the shank of each ear of corn 16. The ear of corn 16 is mounted onto the vertically oriented spindle 108 using the hole drilled in the shank. Thus, using the connection between the hole tapped in the shank of the ear of corn 16 and the vertically oriented spindle, the ear of corn 16 may be handled, oriented and positioned at and/or between stations 104, 106 by automation using transport means 102.

Method

Also disclosed by the present invention is a method for preparing an ear of corn 16 for being handled, positioned and oriented by automated means, including semi and fully automated processes and/or systems. Generally, the method includes providing a station for altering an ear of corn and keeping the ear of corn in a desired position and orientation at the station. In one aspect, altering the ear of corn includes one or both of the steps of removing tissue from the ear of corn to provide for automated handling, positioning and/or orienting of the ear of corn, or appending material to the ear of corn to provide for automated handling, positioning and/or orienting of the ear of corn 16. Steps contemplated for removing tissue include, but are not limited to, scraping tissue from the ear of corn, eroding tissue from the ear of corn, or cutting tissue from the ear of corn. In the case where material, such as ear tissue, is removed from the ear of corn, any of the aforementioned concepts may be used to create a hole or void in the ear of corn or clear tissue from a portion of the ear to provide a spot for holding the ear of corn. Boring a hole in the shank of the ear of corn or removing tissue (i.e., kernels) from the ear of corn may be accomplished specifically by using a drill bit, router bit, forstner bit, hollow boring tube, liquid jet cutter, or chisel. According to one aspect of the present invention, a pneumatically actuated drill 30 (see FIG. 4) may be used to create a hole in the shank of the ear of corn 16. In the preferred method, the present invention provides for automated handling, positioning and/or orienting the ear of corn using the hole created in the ear of corn 16. Tissue extracted or removed from the ear of corn 16 may be evacuated from the station using a vacuum in operative communication with the means for holding the ear of corn or the means for removing/extracting tissue from the ear of corn. In the case where material is being appended to an ear of corn, the method may include an automated device adapted to append a member or material to the ear of corn to provide for automated positioning, handling and/or orienting of the ear of corn using the appended material or member. Various types of materials or members could be appended to the ear of corn whereby some automated system could use the appended materials or members to position, handle and/or orient the ear of corn. Materials such as magnetically active coatings could be applied to a portion of the ear of corn (i.e., the shank portion) whereby an automated process or system uses the coating to grip or hold onto the ear of corn. Alternatively, rigid members or devices such as spindle 108, post, nail, or screw could be inserted into a portion of the ear of corn whereby some automated system could use the rigid member or device to position, handle and/or orient the ear of corn. Automated means for appending, inserting, applying or connecting such materials as a magnetically active coating and/or rigid members or devices such as a screw, post, spindle or nail may be use for manipulating the ear of corn at each station. Methods contemplated for keeping the ear of corn in the desired position and orientation at the station include, but are not limited to, supporting, gripping, holding, stabilizing or retaining the ear of corn to keep the ear of corn in a desired position and orientation at the station and relative to the altering means. One method for keeping the ear of corn in the desired position and orientation at the station may include exposing a portion of the ear of corn (i.e., the shank portion) to positive or negative pressure or forces. Keeping the ear of corn in the desired position and orientation may include positive pressure mechanical devices such as grips, clamps, irises, a chuck, an expandable bladder or any other mechanical means for gripping or holding an ear of corn by the shank or some other portion of the ear. Negative pressure or vacuum pressure may also be used to keep the ear of corn in a desired position and orientation. One example of a pneumatic holding means is illustrated FIGS. 1-3, which show a conofrustical recess 20. Recess 20 is in operable communication with a vacuum to provide negative pressure or a vacuum force at the conofrustical recess 20 for retaining the ear of corn 16 in a desired position and orientation. Contemplation has also been given to holding means, such as support device that includes one or more support members for resting the ear of corn thereon. For example, rails, tubing or other guide members could be used to orient and keep the ear of corn in a desired position and orientation at apparatus 10 during altering. In the preferred form, the holding means as best illustrated in FIGS. 1-3 provides automated high-throughput positioning and orienting of ears of corn to help facilitate an alteration process whereby tissue is removed or material is appended to the ear of corn 16 to provide for automated handling, positioning and/or orienting of the ear of corn 16.

As shown in FIG. 5, methods of the present invention may be used in combination with an automated system or process. Automated system 100 may be configured for processing, testing or sampling an ear of corn 16. System 100 may also be configured for preparing the ear of corn 16 for processing, testing or sampling. In the preferred configuration, automated system 100 would include some type of ear moving means 102 for moving and positioning corn at and between one or more work or processing stations 104 and 106. Alterations made to the ear of corn 16 are configured to work in concert with the moving means 102, such as for example, where the ear moving means 102 includes one or more features adapted to make use of the cavity, added material or appended structure to handle, position and/or orient the ear of corn 16 by automation.

FIGS. 1-5 illustrate exemplary methods configured to accomplish one or more of the objects, features or advantages of the present invention. The method includes using apparatus 10 for tapping a hole into the shank or cob portion of an ear of corn 16. Apparatus 10 generally comprises a cabinet 12 upon which is mounted a control panel 40 and a conofrustical recess 20 having a drill cuttings suction port 22. Within the interior of the cabinet 12, as shown in FIG. 4, is a drill 30 for drilling ear of corn 16 and piston 32 for advancing bit 36 into the shank or cob of each of corn 16.

The conofrustical recess 20 has a cropped cone shape, as best shown in FIGS. 2 and 3, for auto-centering the ear of corn 16 relative to drill 30. The drill cuttings suction port 22, as shown in FIG. 3, is in operative communication with the conofrustical recess 20 so that as suction is provided at the drill cuttings suction port 22 the pressure differential is communicated to the conofrustical recess 20 thereby holding the ear of corn 16 in place using vacuum. The drill cuttings suction port 22 removes cuttings and other debris from the conofrustical recess 20 as it is removed from the ear of corn 16 during the drilling process.

One exemplary method of the present invention for preparing an ear of corn 16 for being handled, positioned and oriented by automation includes inserting an ear of corn 16 shank first into the conofrustical recess 20 for auto-centering the ear of corn 16 relative to the drill 30, retaining the ear of corn 16 within the conofrustical recess 20 by vacuum, and automatically advancing the drill 30 and bit 36 into the shank of the ear of corn 16 for tapping a hole in the shank of the ear of corn 16. The method also includes pneumatically actuating and advancing the drill 30 into the conofrustical recess 20 for tapping the hole in the shank or cob portion of each ear of corn 16. Pneumatic advancement of drill 30 is provided by pneumatic piston 32 that is operated by a local or remotely positioned source, such as a compressor. Pneumatic piston 32 is of the type that is commercially available. Drill 30 is preferably a pneumatic drill (e.g., PAR-A-MATIC self-feed drill, model no. 8255-A, Winnipeg, Manitoba, Calif.). Although a pneumatic drill is preferred, the present invention contemplates substitution of other boring devices, such as an electric or hydraulic drill or impacting device, and including those previously described. Activating the free-hand safety switch 44 and tripping the sensor allows activation and advancement of the drill 30 and bit 36 into the shank of the ear of corn 16. The sensor (not shown) is tripped by inserting the ear of corn 16 into the conofrustical recess 20, which in-turn activates drill cuttings suction port 22, which by vacuum pressure helps retain the ear of corn 16 within the conofrustical recess 20 and evacuates cuttings from the drill 30 passing into the shank of the ear of corn 16. In one embodiment, vacuum pressure supplied to the conofrustical recess 20 is continuously on, but at a pressure that allows manual or automated placement and removal of the ear of corn 16. In an alternative embodiment, drill 30 cycles and the vacuum pressure supplied to the conofrustical recess 20 is turned off which allows the operator to remove the ear of corn 16 from the conofrustical recess 20 without the opposing vacuum force acting on the ear of corn 16. The method of preparing an ear of corn 16 for being handled, positioned and oriented by automation could be in combination with an automated machine or system for testing, sampling and/or preparing the ear of corn 16 for testing and/or sampling. The automated machine, such as automated system 100 shown in FIG. 5, may include a chain-on-edge conveyor spindle or drive 110 wherein the ear of corn 16 is automatically handled, positioned and oriented by insertion of the spindle 108 into the hole in the shank of the ear of corn 16.

It should be appreciated that by using one method of the present invention, material removed or extracted from the ear of corn, such as for example where a hole is drilled in the shank of the ear, allows the ear of corn 16 to be handled, positioned and/or oriented in a high-throughput system, which in-turn allows for testing, sampling and/or preparing the ear of corn 16 for testing and/or sampling. In one aspect, this could include the high-throughput system having an automated transport means 102, such as for example an automated transport means 102 having a spindle 108 for handling, positioning and/or orienting the ear of corn 16 by impaling the ear of corn 16 on the spindle 108 using the hole in the shank of the ear of corn 16. In the case where material is appended to the ear of corn 16, automated transport means 102 may be configured to grip or hold the material, such as a post or spindle, attached to the ear of corn 16. The automated transport means 102 may be configured to pass the ears of corn 16 through one or more processing stations 104, 106. These stations 104, 106 could include any station or subsystem providing automated processing, testing, and sampling of the ear of corn 16, as well as any station or subsystem adapted for preparing the ear of corn 16 for processing, testing and/or sampling. As shown and described in Provisional Application Ser. No. 61/090,979, filed Aug. 22, 2008, entitled "High Throughput Automated Apparatus, Method and System for Coating Ears of Corn," processing stations 104, 106 could include an automated ear coating station for coating each ear of corn 16 with a magnetically active coating and an automated drying station for curing the coating. Processing stations 104, 106 could also include any station or subsystem providing automated positioning of the coated kernels for seed testing. The identification of each ear of corn 16 could be tracked individually or collectively. For example, one ear of corn 16 in each batch being processed could receive an identification tag for identifying the entire batch. Alternatively, each ear of corn 16 could be individually tagged for providing identification of each ear of corn 16 during processing or preparing the ear of corn 16 for processing.

System

Also disclosed by the present invention is a system for automated handling, positioning and/or orienting of an ear of corn 16. The system for automated handling, positioning and/or orienting of an ear of corn includes a station for altering a portion of an ear of corn and altering means for removing tissue from or appending material to the ear of corn 16 to facilitate automated handling, positioning and/or orienting of the ear of corn. The system 100 may include one or more stations automatically processing, testing, sampling and/or preparing the ear of corn for automated processing, testing and/or sampling. Transport means 102 may also be provided for automatically moving ears of corn 16 from station to station (see generally 104 and 106). The transport means 102 is configured for using the altered portion of the ear of corn to handle, position and orient the ear of corn at and between stations 104 and 106. In a preferred form, the altering means of the system 100 includes, but is not limited to, material removal means operatively supported at the station, holding means for positioning and orienting the ear of corn relative to the material removal means, and actuation means for moving said holding means or material removal means for removing tissue from the portion of the ear of corn. The system contemplates altering means having material appending means operatively supported at the station, holding means for positioning and orienting the ear of corn relative to the material appending means, and actuation means for moving the holding means or material appending means for appending material to a portion of the ear of corn 16. The system may include any semi- or fully-automated station adapted for processing, testing or sampling the ear of corn and/or preparing the ear of corn for processing, testing and/or sampling. Moving ears of corn at and between stations of system 100 could be accomplished by transport means, such as a shuttle, a carriage or a conveyor. One type of conveyor is shown in FIG. 5, such as a chain-on-edge conveyor spindle or drive 102.

FIG. 5 illustrates an exemplary system of the present invention. One example of the system includes apparatus 10 for automated tapping of a hole in the shank of the ear of corn 16, one or more stations 104, 106 for automatically processing, testing, sampling and/or preparing the ear of corn 116 for processing, testing and/or sampling, and some automated transport means 102 for automatically moving ears of corn 16 from station to station 104, 106. In the preferred form, the automated transport means 102 uses alterations made to the ear of corn 16, such as a hole tapped in the shank of the ear of corn 16 to handle, position and orient the ear of corn 16 at and between stations 104, 106. The system includes apparatus 10 as described above. Apparatus 10 includes, but is not limited to, a drill 30 operatively supported within a cabinet 12, a conofrustical recess 20 at the cabinet 12 and adapted for auto-centering the ear of corn 16 relative to the drill 30, a vacuum assist system in operative communication with the conofrustical recess 20 for retaining the ear of corn 16 by vacuum pressure, and some actuation means for advancing the drill 30 and bit 36 into the shank of the ear of corn 16 for tapping a hole in the shank of the ear.

The present invention contemplates that the system 100 may include one or more processing stations 104, 106 through which automated transport means 102 passes. The stations 104 and 106 may include any station or subsystem providing automated processing, testing, and sampling of the ear of corn 16. Stations 104 and 106 could also be configured to prepare the ear of corn 16 for processing, testing and/or sampling. Processing stations 104, 106 could include an automated ear coating station for coating each ear of corn 16 with a magnetically active coating and an automated drying station for curing the coating. Processing stations 104, 106 could also include any station or subsystem providing automated positioning of the coated kernels for seed testing, such as shown and illustrated in application Ser. Nos. 12/336,084 and 11/939,402, filed Dec. 16, 2008 and Nov. 13, 2007, respectively, which applications are assigned to the owner of the present application and are incorporated by reference herein in their entirety. The automated transport means 102 could include a shuttle, a carriage or a conveyor such as a chain-on-edge conveyor spindle or drive 110. Using the hole prepared in the shank of the ear of corn 16, the automated transport means 102 handles, orients and positions the ear of corn 16 as needed for each of the processes occurring at stations 104, 106. For example, the automated transport means 102 may be a chain-on-edge conveyor spindle 110 as shown in FIG. 5. Each ear of corn 16 is impaled onto a spindle 108 by inserting the spindle 108 into the hole in the shank of the ear of corn 16. The ear of corn 16 is then shuttled through various types of processing stations 104, 106 of the system 100 for preparing or testing the ear of corn 16 and/or kernels on the ear of corn 16. These processing stations could include stations 104, 106 that prepare each ear of corn 16 for automated seed sampling processes, such as for example, where each kernel of corn is magnetically oriented by magnetic attenuation using a magnetically active coating applied to and cured on the crown of each kernel using stations 104, 106. In the case where material or some member is appended to the ear of corn 16, such as a post, nail, screw, hook, spindle or other rigid structural member, provisions may be configured into the transport means for working in cooperation with the appended material or member for providing automated handling, positioning and/or orienting the ear. For example, in the case where a post is appended to the ear of corn, the automated transport means 102 may include a socket adapted to receive the post to provide handling, positioning and orienting of the ear 16 by automation.

The embodiments of the present invention have been set forth in the drawings and specification and although specific terms are employed, these are used in a generically descriptive sense only and are not used for purposes of limitation. Changes in the formed proportion of parts, as well as any substitutions of equivalences are contemplated as circumstances may suggest or are rendered expedient without departing from the spirit and scope of the invention as further defined in the following claims.

What is claimed is:

1. A method for preparing an ear of corn for being handled, positioned and oriented by automated means, the method comprising:
   providing a station for altering an ear of corn;
   auto-centering the ear of corn at the station;
   retaining the ear of corn in a desired position and orientation at the station for altering the ear of corn; and
   altering the ear of corn comprising:
   a. removing tissue from the ear of corn to provide for automated handling, positioning and orienting of the ear of corn; or
   b. appending material to the ear of corn to provide for automated handling, positioning and orienting of the ear of corn.

2. The method of claim 1 wherein removing tissue step comprises:
   a. scraping tissue from the ear of corn;
   b. eroding tissue from the ear of corn; or
   c. cutting tissue from the ear of corn.

3. The method of claim 1 wherein removing tissue step comprises creating a hole in a shank portion of the ear of corn.

4. The method of claim 3 further comprising automated handling, positioning and orienting the ear of corn using the hole.

5. The method of claim 1 wherein the appending material step comprises appending a rigid member to the ear of corn.

6. The method of claim 5 further comprising automated handling, positioning and orienting the ear of corn using the rigid member attached to the ear of corn.

7. The method of claim 1 wherein the step of retaining the ear of corn in the desired position and orientation at the station comprises:
   a. exposing a shank portion of the ear of corn to positive pressure; or
   b. exposing an shank portion of the ear of corn to negative pressure.

8. The method of claim 1 in combination with an automated machine for testing, sampling or preparing the ear of corn for testing or sampling.

9. The method of claim 8 further comprising handling, positioning and orienting the ear of corn with the automated machine using:
   a. the material appended to the ear of corn; or
   b. the removed tissue portion of the ear of corn.

10. A method for preparing an ear of corn for being handled, positioned and oriented by automation, the method comprising:
    providing a station having material removal means;
    auto-centering the ear of corn at the station;
    retaining the ear of corn in a desired position and orientation at the station by holding means; and
    autonomously creating a hole in the ear of corn with material removal means to provide for automated handling, positioning and orienting of the ear of corn using the hole.

11. The method of claim 10 further comprising creating the hole in the ear of corn by actuating and advancing:
    a. said material removal means into said holding means; or
    b. said holding means into said material removal means.

12. The method of claim 10 wherein the step of creating the hole in the ear of corn with said material removal means comprises:
    a. scraping material from the ear of corn;
    b. eroding material from the ear of corn; or
    c. cutting material from the ear of corn.

13. The method of claim 10 wherein the step of keeping the ear in the desired position and orientation with said holding means comprises:
    gripping the ear of corn pneumatically.

14. The method of claim 10 further comprising detecting presence of the ear of corn at said holding means for controlling operation of said material removal means.

15. The method of claim 10 in combination with an automated machine configured for testing, sampling and preparing the ear of corn for testing and sampling.

16. The method of claim 15 wherein the automated machine comprises a chain-on edge conveyor spindle, each ear of corn being attached to the spindle by impaling the ear of corn on the spindle.

17. A method for automated handling, positioning and orienting of an ear of corn by conveyance means in a high-throughput system, the method comprising:
    providing a station for altering an ear of corn;
    auto-centering the ear of corn at the station;
    holding the ear of corn at the station during altering;
    altering the ear of corn to have a feature used to secure the ear of corn to said conveyance means; and
    handling, positioning and orienting the ear of corn in the high-throughput system using said conveyance means for testing, sampling, processing or preparing the ear of corn for testing, sampling or processing.

18. The method of claim 17 wherein the altering step comprises:
    a. creating a cavity in the ear of corn;
    b. adding material to the ear of corn; or
    c. appending a feature to the ear of corn.

19. The method of claim 18 wherein said conveyance means is adapted to use the cavity, added material or appended structure to handle, position and orient the ear of corn in the high-throughput system.

20. The method of claim 17 further comprising passing the conveyance means holding said ears of corn through one or more corn testing, sampling, or processing stations within the high-throughput system.

21. The method of claim 1, wherein auto-centering the ear of corn at the station comprises inserting the ear of corn into a conofrustical recess.

22. The method of claim 10, wherein auto-centering the ear of corn at the station comprises inserting the ear of corn into a conofrustical recess.

23. The method of claim 17, wherein auto-centering the ear of corn at the station comprises inserting the ear of corn into a conofrustical recess.

* * * * *